US012709687B2

(12) United States Patent
Zahrani et al.

(10) Patent No.: US 12,709,687 B2
(45) Date of Patent: Aug. 18, 2026

(54) CORROSION-RESISTANT ARTICLES AND METHODS FOR MAKING SUCH

(71) Applicant: Saudi Arabian Oil Company, Dhahran (SA)

(72) Inventors: Talal Y. Zahrani, Dhahran (SA); Muthukumar Nagu, Dhahran (SA); Muhammed Imran Ul-Haq, Dhahran (SA); Nayef M. Alanazi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 538 days.

(21) Appl. No.: 18/183,487

(22) Filed: Mar. 14, 2023

(65) Prior Publication Data

US 2024/0309223 A1 Sep. 19, 2024

(51) Int. Cl.

| | |
|---|---|
| ***C09D 5/08*** | (2006.01) |
| ***C07D 213/30*** | (2006.01) |
| ***C08K 5/3432*** | (2006.01) |
| ***C09D 7/20*** | (2018.01) |
| ***C23F 11/14*** | (2006.01) |

(52) U.S. Cl.

CPC ........... *C09D 5/086* (2013.01); *C07D 213/30* (2013.01); *C09D 7/20* (2018.01); *C23F 11/141* (2013.01); *C23F 11/149* (2013.01); *C08K 5/3432* (2013.01)

(58) Field of Classification Search

CPC ..... C09D 5/086; C07D 213/30; C23F 11/141; C23F 11/149

See application file for complete search history.

(56) References Cited

U.S. PATENT DOCUMENTS

| | | | |
|---|---|---|---|
| 2,668,100 A | 2/1954 | Luvisi | |
| 2,736,658 A | 2/1956 | Pfohl et al. | |
| 3,365,477 A | 1/1968 | Gee et al. | |
| 3,981,682 A | 9/1976 | Ward et al. | |
| 4,028,117 A | 6/1977 | Moat | |
| 4,148,605 A | 4/1979 | Andress, Jr. | |
| 4,214,876 A | 7/1980 | Garth et al. | |
| 4,637,899 A | 1/1987 | Kennedy, Jr. | |
| 4,672,118 A | 6/1987 | Fisk et al. | |
| 4,812,263 A | 3/1989 | Login | |
| 5,000,873 A | 3/1991 | Fisk et al. | |
| 5,336,441 A | 8/1994 | Shah et al. | |
| 9,434,911 B2 | 9/2016 | Bennett et al. | |
| 10,563,114 B2 | 2/2020 | Mandal et al. | |
| 10,590,282 B2 | 3/2020 | Balasubramanian et al. | |
| 10,787,745 B2 | 9/2020 | Barmatov et al. | |
| 2008/0308770 A1* | 12/2008 | Tiwari .................. | C23F 11/149 544/335 |

FOREIGN PATENT DOCUMENTS

| | | |
|---|---|---|
| CA | 2196650 A1 | 8/1998 |
| GB | 2532990 A | 6/2016 |

OTHER PUBLICATIONS

U.S. Appl. No. 17/741,960, filed May 11, 2022—Specification and Drawings.

* cited by examiner

*Primary Examiner* — Frank J Vineis
(74) *Attorney, Agent, or Firm* — Dinsmore & Shohl LLP

(57) ABSTRACT

Described herein are corrosion-resistant substrates and methods of producing a corrosion-resistant substrates. In one or more embodiments, a corrosion-resistant substrate may include a substrate including a first surface and a corrosion-resistant film positioned on at least a portion of the first surface of the substrate. The corrosion-resistant film may be solid. In embodiments, the film may include a 1-(2-hydroxyalkyl)pyridinium compound.

15 Claims, 4 Drawing Sheets

CORROSION-RESISTANT ARTICLES AND METHODS FOR MAKING SUCH

TECHNICAL FIELD

The present disclosure relates to corrosion-resistance and, more specifically, to corrosion-resistant materials.

BACKGROUND

Corrosion is an issue for many materials when they interact with their environments over time. For example, the presence of species such as $H_2S$, $CO_2$, organic acids, and brine solutions in produced oil may create a corrosive environment for transportation pipelines and oil processing units in an oil and gas facility. Specifically, when $CO_2$ and $H_2S$ are dissolved in water, these species may behave like weak acids and promote the corrosion of steel, thus resulting in damage to the internal walls of the transportation pipelines and oil processing units and causing leaks that will increase the maintenance time and costs associated with the oil and gas processing. Many conventional compounds may be used in corrosion inhibitors and corrosion-resistant films in order to reduce corrosion of surfaces. However, these conventional compounds are often toxic and non-biodegradable. Additionally, there is a relatively high cost associated with the production of these conventional compounds. Further, these conventional compounds do not sufficiently resist the corrosive effects present in the wet sour environment (i.e., an environment rich in $H_2S$) often present in crude oil processing facilities. As such, new compounds are needed for use in corrosion inhibitors and corrosion-resistant films.

SUMMARY

Described herein are corrosion-resistant films, corrosion-resistant substrates comprising these corrosion-resistant films, and corrosion inhibitor solutions that may be contacted and dried onto surfaces of substrates to create the corrosion-resistant substrates. These corrosion inhibitor solutions and corrosion-resistant films may comprise 1-(2-hydroxyalkyl)pyridinium compounds. The presence of these 1-(2-hydroxyalkyl)pyridinium compounds in these corrosion inhibitor solutions and corrosion-resistant films may, in some embodiments, result in relatively strong bonding between the corrosion-resistant films and the substrates, and/or relatively high corrosion-resistant properties in a wet sour environment when compared to conventional compounds adhered to a substrate or a substrate with no corrosion-resistant film. Further, in some embodiments, using these 1-(2-hydroxyalkyl)pyridinium compounds in the corrosion inhibitor solutions and corrosion-resistant films may reduce the cost associated with the production of corrosion inhibitor solutions and corrosion-resistant films. Also, in some embodiments, these 1-(2-hydroxyalkyl)pyridinium compounds in the corrosion inhibitor solutions and corrosion-resistant films may be less toxic than conventional compounds present in corrosion inhibitor solutions and corrosion-resistant films.

According to one or more embodiments of the present disclosure, a corrosion-resistant substrate may comprise a substrate comprising a first surface and a corrosion-resistant film positioned on at least a portion of the first surface of the substrate. The corrosion-resistant film may be solid. In embodiments, the film may comprise a 1-(2-hydroxyalkyl) pyridinium compound having a general formula:

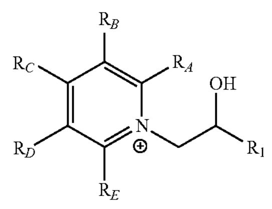

$R_1$ may be a $C_1$-$C_{18}$ alkyl group, a $C_1$-$C_{18}$ hydroxyl alkyl group, a $C_1$-$C_{18}$ alkenyl group, a $C_1$-$C_{18}$ internal alkynl group, a $C_1$-$C_{18}$ acryl group, a $C_1$-$C_{18}$ cycloalkyl group, or a $C_1$-$C_{18}$ functional alkyl group. $R_A$, $R_B$, $R_C$, $R_D$, and $R_E$ may each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group.

According to one or more additional embodiments of the present disclosure, a corrosion inhibitor solution may comprise a solvent and a 1-(2-hydroxyalkyl)pyridinium compound having a general formula:

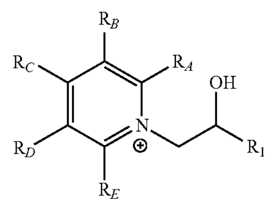

$R_1$ may be a $C_1$-$C_{18}$ alkyl group, a $C_1$-$C_{18}$ hydroxyl alkyl group, a $C_1$-$C_{18}$ alkenyl group, a $C_1$-$C_{18}$ internal alkynl group, a $C_1$-$C_{18}$ acryl group, a $C_1$-$C_{18}$ cycloalkyl group, or a $C_1$-$C_{18}$ functional alkyl group. $R_A$, $R_B$, $R_C$, $R_D$, and $R_E$ may each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group.

According to one or more embodiments of the present disclosure, a method of producing a corrosion-resistant substrate may comprise contacting at least a portion of a first surface of a substrate with a corrosion inhibitor solution. The method may further comprise drying the corrosion inhibitor solution to produce a corrosion-resistant film on the substrate. The corrosion inhibitor solution may, in embodiments, comprise a solvent and a 1-(2-hydroxyalkyl)pyridinium compound. In embodiments, at least a portion of the solvent may be expelled from the corrosion inhibitor solution during drying to form a corrosion-resistant film. The corrosion-resistant film may be solid. The 1-(2-hydroxyalkyl)pyridinium compound may have the general formula:

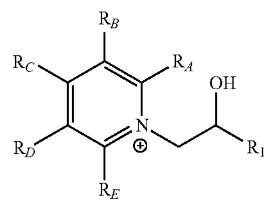

$R_1$ may be a $C_1$-$C_{18}$ alkyl group, a $C_1$-$C_{18}$ hydroxyl alkyl group, a $C_1$-$C_{18}$ alkenyl group, a $C_1$-$C_{18}$ internal alkynl group, a $C_1$-$C_{18}$ acryl group, a $C_1$-$C_{18}$ cycloalkyl group, or a $C_1$-$C_{18}$ functional alkyl group. $R_A$, $R_B$, $R_C$, $R_D$, and $R_E$ may each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group.

These and other embodiments are described in more detail in the detailed description. It is to be understood that both the foregoing general description and the following detailed description present embodiments of the presently disclosed technology, and are intended to provide an overview or framework for understanding the nature and character of the presently disclosed technology as it is claimed. The accompanying drawings are included to provide a further understanding of the presently disclosed technology and are incorporated into and constitute a part of this specification. The drawings illustrate various embodiments and, together with the description, serve to explain the principles and operations of the presently disclosed technology. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and wherein.

DETAILED DESCRIPTION

Embodiments of the present disclosure are directed to corrosion-resistant materials such as corrosion resistant substrates, materials for making such corrosion resistant substrates, and methods for using such corrosion-resistant substrates. In some embodiments, corrosion-resistant films may be applied to substrates, formed from corrosion inhibitor solutions. In embodiments described herein, the corrosion inhibitor solutions and corrosion-resistant films may comprise 1-(2-hydroxyalkyl)pyridinium compounds.

As described herein, corrosion refers to a process in which a material is oxidized by substances in the environment that causes the material to lose electrons and deteriorates at least a portion of the material. The term "corrosion-resistant" generally refers to the resistance that a material has against corrosion. As described herein, corrosion-resistant materials display enhanced resistance to corrosion on the substrates, which may be achieved, as is described in embodiments herein, by forming a barrier over the substrates, thus shielding the substrates from the environment.

Figure 1:
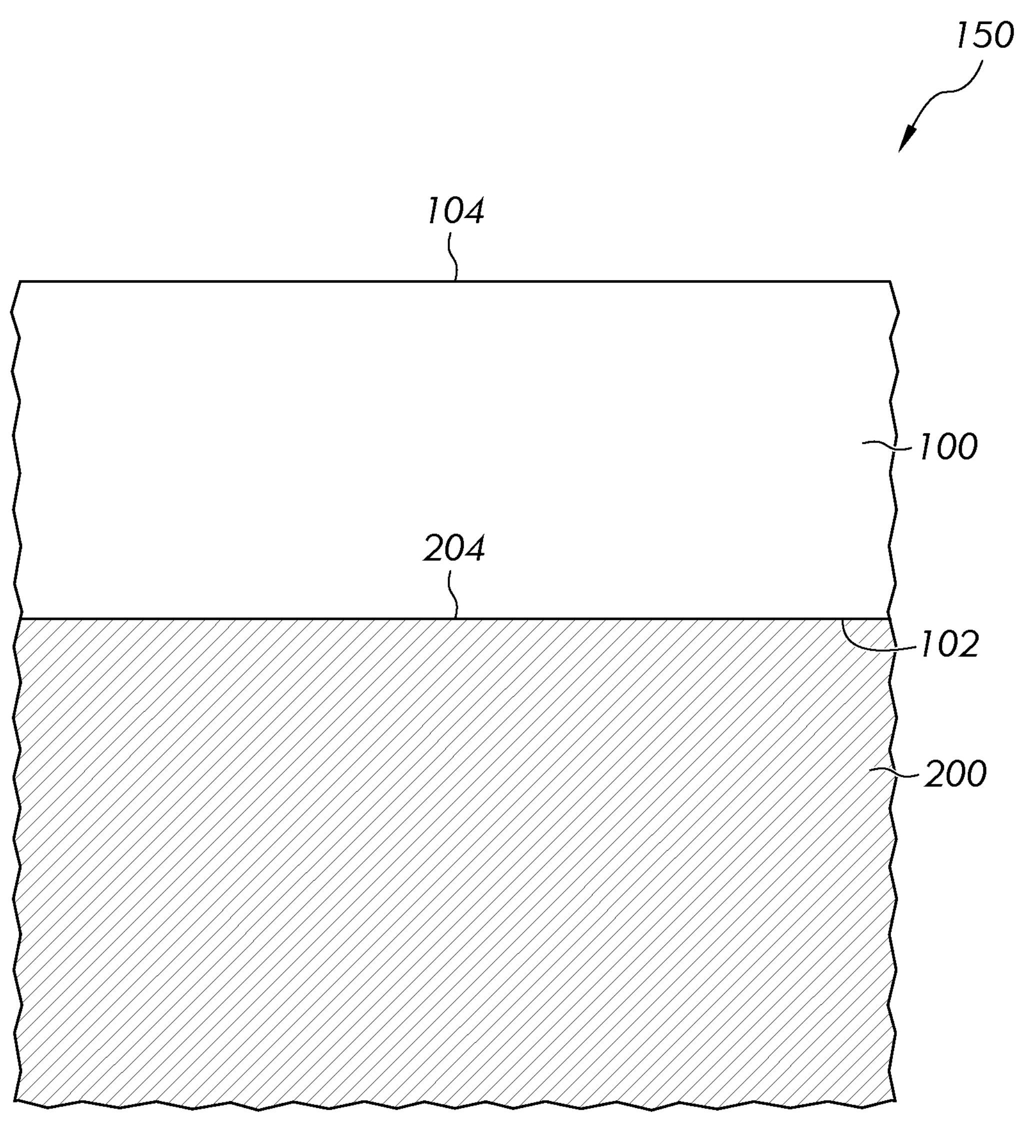
FIG. 1 schematically depicts a cross-sectional view of a substrate comprising a corrosion-resistant film, according to one or more embodiments shown and described herein.

Referring now to FIG. 1, according to one or more embodiments, the corrosion-resistant substrates 150 may comprise a substrate 200 that may comprise at least a first surface 204. The term "substrate" may refer to any object with at least one surface where a solution may contact and form a film that remains on at least a portion of that surface. The corrosion-resistant substrates 150 may also comprise a corrosion-resistant film 100 that comprises at least a first surface 102 and a second surface 104 opposite the first surface 102. The corrosion-resistant film 100 may be positioned on at least a portion of the first surface 204 of the substrate 200. As depicted, the corrosion-resistant substrates 150 may have the first surface 102 of the corrosion-resistant film 100 positioned on and in direct contact with at least a portion of the first surface 204 of the substrate 200. The second surface 104 of the corrosion-resistant film 100 may be an "air-side" surface defining the outer edge of the corrosion-resistant substrate 150.

In one or more embodiments, the corrosion-resistant film 100 may be a solid. The term "solid" may refer to a material that is generally firm, stable in shape, and is not a liquid or a fluid. Accordingly, when the corrosion-resistant film 100 is a solid, the first surface 102 of the corrosion-resistant film 100 adheres to the first surface 204 of the substrate 200 so that the corrosion-resistant film 100 remains on the substrate 200 and holds its shape while the substrate 200 and/or the corrosion-resistant film 100 is moved.

In one or more embodiments, the corrosion-resistant film 100 has a thickness of from 0.1 nm to 1,000 nm, such as a thickness of from 0.1 nm to 900 nm, from 0.1 nm to 800 nm, from 0.1 nm to 700 nm, from 0.1 nm to 600 nm, from 0.1 nm to 500 nm, from 0.1 nm to 400 nm, from 0.1 nm to 300 nm, from 0.1 nm to 200 nm, from 0.1 nm to 100 nm, from 1 nm to 1,000 nm, from 10 nm to 1,000 nm, from 50 nm to 1,000 nm, from 100 nm to 1,000 nm, from 200 nm to 1,000 nm, from 300 nm to 1,000 nm, from 400 nm to 1,000 nm, from 500 nm to 1,000 nm, from 600 nm to 1,000 nm, from 700 nm to 1,000 nm, from 800 nm to 1,000 nm, from 900 nm to 1,000 nm, from 10 nm to 900 nm, from 100 nm to 800 nm, from 200 nm to 700 nm, or from 300 nm to 600 nm.

Figure 2:
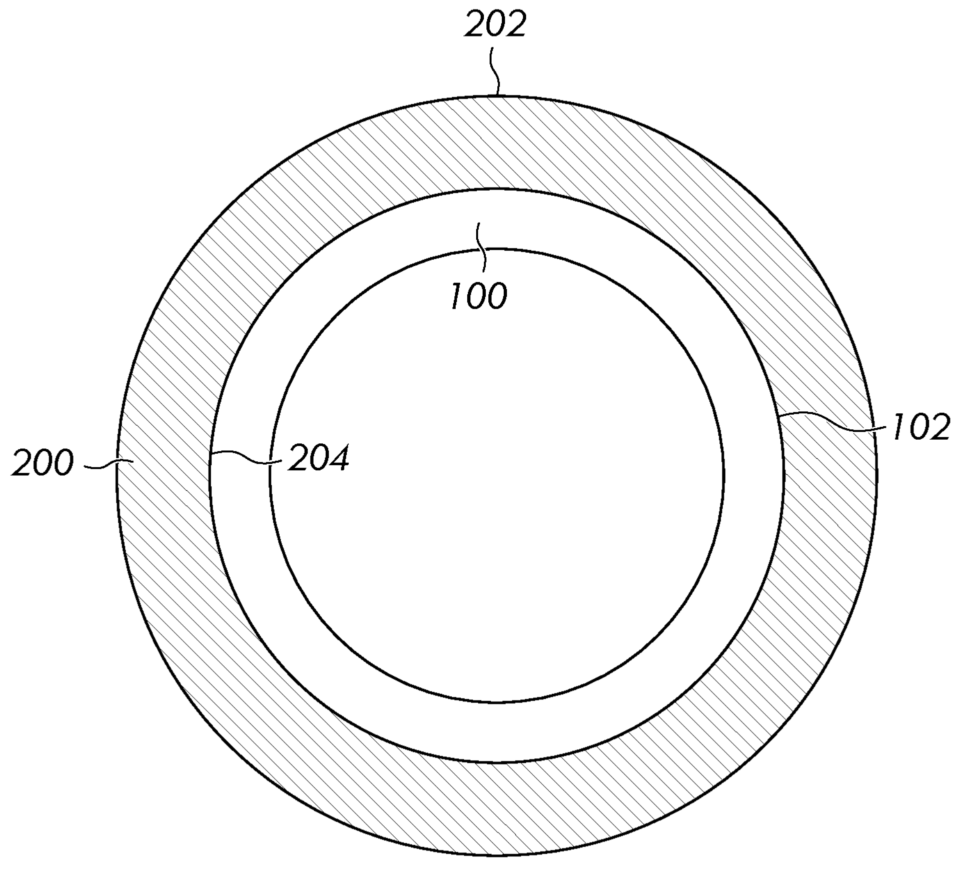
FIG. 2 schematically depicts a cross-sectional view cut in the axial direction of a metal pipe comprising a corrosion-resistant film, according to one or more embodiments shown and described herein.

Now, referring to FIG. 2, in one or more embodiments, the substrate 200 of the corrosion-resistant substrates may be a metal pipe that comprises at least a first surface 204 and a second surface 202. The term "pipe" may refer to a tubular hollow cylinder having a circular, or near circular, cross section that is used to transport substances (for example liquids, gases, slurries, powders, small solids, etc.). The metal pipe may comprise one or more metals and one or more surfaces of the metal pipe may comprise metal oxides. For example, the metal pipe may comprise carbon steel. In some embodiments, the first surface 204 of the metal pipe may be the internal surface of the metal pipe, and the pipe may further comprise an outer surface 202. The term "internal surface" may refer to the surface of the inside of the metal pipe that is enclosed within the tubular cylinder of the metal pipe. For example, when the substrate 200 is a metal pipe and the first surface 204 is the internal surface of the metal pipe, the first surface 102 of the corrosion-resistant film 100 may be in direct contact with the internal surface of the metal pipe. Without being bound by a theory, it is believed that the corrosion-resistant film 100 being in direct contact with a least a portion of the internal surface of the metal pipe creates a barrier between the substances that flow through the metal pipe and the internal surface of the metal pipe.

According to one or more embodiments, the corrosion inhibitor solutions and corrosion-resistant films may comprise a 1-(2-hydroxyalkyl)pyridinium compound having the structure of Chemical Structure #1.

Chemical Structure #1

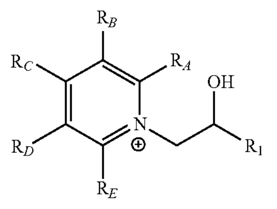

Referring to Chemical Structure #1, the general structure includes $R_1$, $R_A$, $R_B$, $R_C$, $R_D$, and $R_E$ that each represent various functional groups that can be included in the 1-(2-hydroxyalkyl)pyridinium compound. $R_1$ may be a $C_1$-$C_{18}$ alkyl group, a $C_1$-$C_{18}$ hydroxyl alkyl group, a $C_1$-$C_{18}$ alkenyl group, a $C_1$-$C_{18}$ internal alkynl group, a $C_1$-$C_{18}$ acryl group, a $C_1$-$C_{18}$ cycloalkyl group, or a $C_1$-$C_{18}$ functional alkyl group. $R_A$, $R_B$, $R_C$, $R_D$, and $R_E$ may each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group. Without being bound by a theory, it is believed that one or more of $R_1$, $R_A$, $R_B$, $R_C$, $R_D$, and $R_E$ having a relatively long carbon chain moiety allows the corrosion-resistant film produced from the corrosion inhibitor solution to better adhere to the surface of a substrate. Further, if the carbon chain moiety has greater than 18 carbon atoms, there is an increased risk of the corrosion-resistant film being removed from the surface of the substrate.

In one or more embodiments, the term "functional group" or "group" may refer to a substituent or moiety that is present in the 1-(2-hydroxyalkyl)pyridinium compound. For example, when the disclosure states that $R_1$ may be a methyl group, the methyl group ($-CH_3$) replaces $R_1$ of the general structure of the 1-(2-hydroxyalkyl)pyridinium compound, where the carbon atom of the methyl group is now bonded to the carbon atom of the 1-(2-hydroxyalkyl)pyridinium compound to which $R_1$ bonded.

As described herein, moieties may be defined by the number of carbon atoms included in the moiety, such as $C_x$-$C_y$, where x is the least number of carbon atoms and y is the greatest number of carbon atoms contemplated. For example, $C_1$-$C_{18}$ describes a moiety that has from 1 to 18 carbon atoms.

In some embodiments, $R_1$, $R_A$, $R_B$, $R_C$, $R_D$, and $R_E$ may each independently be a $C_1$-$C_{18}$ alkyl group. The term "alkyl group" refers to a functional group that only contains carbon and hydrogen atoms where the carbon atoms and hydrogen atoms are only connected by single bonds. In some embodiments, $R_1$, $R_A$, $R_B$, $R_C$, $R_D$, and $R_E$ may each independently be a straight chained alkyl group having the chemical formula $-(CH_2)_xCH_3$, where x is from 0 to 17, such as 0 (a methyl group), 1, 2, 3, 4, 5, 6, 7, 8, 9, 10, 11, 12, 13, 14, 15, 16, 17, or 18 carbon atoms. In additional embodiments, $R_1$, $R_A$, $R_B$, $R_C$, $R_D$, and $R_E$ may each independently be branched alkyl groups having from 3 to 18 carbon atoms, such as 3, 4, 5, 6, 7, 8, 9, 10, 11, 12, 13, 14, 15, 16, 17, or 18 carbon atoms. In some embodiments, the alkyl group may include a ring structure, such as a pentane ring, a hexane ring, etc.

In some embodiments, $R_1$, $R_A$, $R_B$, $R_C$, $R_D$, and $R_E$ may each independently comprise a $C_1$-$C_{18}$ hydroxyl alkyl group.

The term "hydroxyl alkyl group" refers to a functional group that includes one or more a hydroxyl moieties ($-OH$) bonded to an alkyl group. According to embodiments, the hydroxyl alkyl group may include 1, 2, 3, 4, 5, or even more hydroxyl moieties. In some embodiments, $R_1$, $R_A$, $R_B$, $R_C$, $R_D$, and $R_E$ may each independently be a straight chained hydroxyl alkyl group having the chemical formula $-(CH_2)_xOH$, where x is from 1 to 18. In additional embodiments, $R_1$, $R_A$, $R_B$, $R_C$, $R_D$, and $R_E$ may each independently be branched hydroxyl alkyl groups having from 1 to 18 carbon atoms and at least one hydroxyl group.

In some embodiments, $R_1$, $R_A$, $R_B$, $R_C$, $R_D$, and $R_E$ may each independently comprise a $C_1$-$C_{18}$ alkenyl group. The term "alkenyl group" refers to a functional group consisting of hydrogen and carbon atoms where at least two carbon atoms have a double bond. In some embodiments, the alkenyl group may have a single carbon to carbon double bond that is at the end of moiety (i.e., having the structure $-(CH_2)_xCH{=}CH_2$, where x is from 0 to 16, such as 0, 1, 2, 3, 4, 5, 6, 7, 8, 9, 10, 11, 12, 13, 14, 15, or 16).

In some embodiments, $R_1$, $R_A$, $R_B$, $R_C$, $R_D$, and $R_E$ may each independently comprise a $C_1$-$C_{18}$ alkynl group. The term "alkynyl group" refers to a functional group consisting of hydrogen and carbon atoms where at least two carbon atoms have a triple bond. In some embodiments, $R_A$, $R_B$, $R_C$, $R_D$, and $R_E$ may each independently have a single carbon to carbon triple bond that is at the end of moiety (i.e., having the structure $-(CH_2)_xC{\equiv}CH$, where x is from 0 to 16, such as 0, 1, 2, 3, 4, 5, 6, 7, 8, 9, 10, 11, 12, 13, 14, 15, or 16).

In some embodiments, $R_1$, $R_A$, $R_B$, $R_C$, $R_D$, and $R_E$ may each independently comprise one or more of a carbon-carbon double bond, a carbon-carbon triple bond, or a combination thereof, provided that $R_1$ does not comprise a terminal alkyne.

In some embodiments, $R_1$, $R_A$, $R_B$, $R_C$, $R_D$, and $R_E$ may each independently be a $C_1$-$C_{18}$ acryl group. The term "acryl group" refers to a functional group consisting of a carbon-carbon double bond and a carbon-oxygen double bond separated by a carbon-carbon single bond. The acryl group may have the general formula $-(CH_2)_nCOCHCH_2$, where n is any integer from 0 to 15, such as 0, 1, 2, 3, 4, 5, 6, 7, 8, 9, 10, 11, 12, 13, 14, or 15.

In some embodiments, $R_1$, $R_A$, $R_B$, $R_C$, $R_D$, and $R_E$ may each independently be a $C_1$-$C_{18}$ functional alkyl group. The term "functional alkyl group" refers to an alkyl group which includes at least one moiety bonded to any carbon atom of the alkyl group. In some embodiments, the functional alkyl group may comprise more than one of the same moiety. In some embodiments, the functional alkyl group may comprise two or more different moieties. In some embodiments, the functional alkyl group may comprise a moiety chosen form a carboxyl group (i.e., $-COOH$), an amine group (i.e., $-NH_2$), or a thiol group (i.e., $-SH$).

In some embodiments, $R_1$ may be a $C_2$-$C_{17}$ alkyl group, and $R_A$, $R_B$, $R_C$, $R_D$, and $R_E$ may each be hydrogen. For example, $R_1$ may be a $C_4$-$C_{16}$ alkyl group, a $C_6$-$C_{14}$ alkyl group, or a $C_8$-$C_{12}$ alkyl group. In some embodiments, $R_1$ may be a $C_1$-$C_{17}$, a $C_1$-$C_{16}$, a $C_1$-$C_{18}$, a $C_1$-$C_{14}$, a $C_1$-$C_{13}$, a $C_1$-$C_{12}$, a $C_1$-$C_{11}$, a $C_1$-$C_{10}$, a $C_1$-$C_9$, a $C_1$-$C_8$, a $C_1$-$C_7$, a $C_1$-$C_6$, a $C_1$-$C_5$, a $C_1$-$C_4$, a $C_1$-$C_3$, or a $C_1$-$C_2$ alkyl group. In some embodiments, $R_1$ may be a $C_2$-$C_{18}$, $C_3$-$C_{18}$, $C_4$-$C_{18}$, $C_5$-$C_{18}$, $C_6$-$C_{18}$, $C_7$-$C_{18}$, $C_8$-$C_{18}$, $C_9$-$C_{18}$, $C_{10}$-$C_{18}$, $C_1$-$C_{18}$, $C_{12}$-$C_{18}$, $C_{13}$-$C_{18}$, $C_{14}$-$C_{18}$, $C_{15}$-$C_{18}$, $C_{16}$-$C_{18}$, or $C_{17}$-$C_{18}$ alkyl group. In one embodiment, $R_1$ may be a $C_{10}$ alkyl group (i.e., a decyl group) and $R_A$, $R_B$, $R_C$, $R_D$, and $R_E$ may each be hydrogen. In one embodiment, $R_1$ may be a $C_{12}$ alkyl group (i.e., a dodecyl group) and $R_A$, $R_B$, $R_C$, $R_D$, and $R_E$ may each be hydrogen.

Without being bound by a theory, it is believed that the 1-(2-hydroxyalkyl)pyridinium compound has relatively strong bonding to a metal surface due to both the physiorption and chemisorption of multiple parts of the pyridinium hydroxalkyl compound and the metal surface. The term "physiorption" refers to the physical bonding of liquid molecules onto a material's surface. Van der Waal interactions, or similar interactions, between atoms on the surface of a metal may cause these surface atoms to be reactive, thus causing them to attract molecules to satisfy the atomic force imbalance. It is believed that the presence of the positively-charged nitrogen atom of the 1-(2-hydroxyalkyl)pyridinium compound forms strong Van der Waal, or similar, interactions with the metal surface. The term "chemisorption" refers to the adsorption between a surface and an adsorbate due to chemical bonding. Multiple parts of the 1-(2-hydroxyalkyl) compound including, but not limited to, the hydroxyl group and pyridinium group, may bond with the metal surface. It is believed that due to the increased number of functional groups on the 1-(2-hydroxyalkyl)pyridinium compound that can interact with a metal surface through physiorption and/or chemisorption, the corrosion-resistant film 100 that comprises the 1-(2-hydroxyalkyl)pyridinium compound forms stronger interactions and bonds with a metal surface and, thus, provides the metal surface with a stronger and longer lasting corrosion-resistant film 100 than many conventional films that use conventional compounds for resisting corrosion on a metal surface.

The present disclosure is also directed to methods of producing corrosion-resistant substrates 150 and various embodiments of corrosion inhibitor solutions. The methods of producing corrosion-resistant substrates 150 may comprise contacting at least a portion of a first surface 204 of a substrate 200 with a corrosion inhibitor solution, where the corrosion inhibitor solution comprises a solvent and the 1-(2-hydroxyalkyl)pyridinium compound described herein. Then, the methods may further comprise drying the corrosion inhibitor solution to produce the corrosion-resistant film 100 on the substrate 200, where at least a portion of the solvent is expelled from the corrosion inhibitor solution during the drying to form the solid corrosion-resistant film 100. For example, when the substrate 200 is a pipe and the first surface 204 is the internal surface of the pipe, the corrosion inhibitor solution is adhered on the internal surface of the pipe and the corrosion inhibitor solution dries on the internal surface of the pipe to form the solid corrosion-resistant film 100 on the internal surface of the pipe.

In one or more embodiments, the corrosion inhibitor solution may comprise a solvent and a 1-(2-hydroxyalkyl) pyridinium compound, as described herein. In some embodiments, the solvent may comprise water, an alcohol, aromatic naphtha, or combinations thereof.

According to one or more embodiments, the corrosion inhibitor solution may comprise from 1 wt. % to 50 wt. % of the 1-(2-hydroxyalkyl)pyridinium compound. In some embodiments, the corrosion inhibitor solution may comprise from 1 wt. % to 45 wt. %, from 5 wt. % to 40 wt. %, from 10 wt. % to 35 wt. %, or from 15 wt. % to 30 wt. %, or 15 wt. % to 25 wt. % of the 1-(2-hydroxyalkyl)pyridinium compound. In some embodiments, the corrosion inhibitor solution may comprise from 5 wt. % to 50 wt. %, 5 wt. % to 40 wt. %, 5 wt. % to 35 wt. %, 5 wt. % to 30 wt. %, 5 wt. % to 25 wt. %, 5 wt. % to 20 wt. %, 5 wt. % to 15 wt. %, or 5 wt. % to 10 wt. %, of the 1-(2-hydroxyalkyl)pyridinium compound.

In some embodiments, drying the corrosion inhibitor solution in order to produce the solid corrosion-resistant film 100 may include passively drying the corrosion inhibitor solution. Passively drying the corrosion inhibitor solution may refer to allowing the corrosion inhibitor solution to dry on the first surface 204 of the substrate 200 without the use of an external heat source. For example, the corrosion inhibitor solution may be allowed to dry at room temperature after contacting the first surface 204 of the substrate 200 or any similar method where the corrosion inhibitor solution is not heated with an external heat source. Further, drying the corrosion inhibitor solution in order to produce the solid corrosion-resistant film 100 may include heating the corrosion inhibitor solution with a heat source. Heating the corrosion inhibitor solution with a heat source may refer to any method where heat from an outside source is transferred to the corrosion inhibitor solution and the first surface 204 of the substrate 200 in order to dry the corrosion inhibitor solution. For example, a heat lamp may be directed onto the corrosion inhibitor solution and the first surface 204 of the substrate 200 in order to accelerate the drying time of the corrosion inhibitor solution. In another example, external processing units, liquids, or gases may transfer heat to the corrosion inhibitor solution and the first surface 204 of the substrate 200 in order to accelerate the drying time of the corrosion inhibitor solution. In some embodiments, the drying of the corrosion inhibitor solution in order to produce the solid corrosion-resistant film 100 may include both passively drying the corrosion inhibitor solution and heating the corrosion inhibitor solution with a heat source.

EXAMPLES

Examples are provided herein which may disclose one or more embodiments of the present disclosure. However, the Examples should not be viewed as limiting on the claimed embodiments hereinafter provided.

Example 1—Synthesis of 1-(2-Hydroxydodecyl)Pyridinium Chloride

Pyridine (1.5 mmol) and hydrochloric acid (1 mmol) were added to a round bottom flask, purged with nitrogen, and stirred at room temperature (25° C.) for 10 minutes. Then, 1,2-epoxydodecane (1 mmol) was added to the flask along with a volume of water equivalent to the volume of the added hydrochloric acid. The reaction mixture was stirred again for 30 minutes, then heated to 100° C. for 15 hours. At the end of the elapsed time, the excess pyridine was removed from the final solution via rotary evaporation. Diethyl ether was added to precipitate the final 1-(2-hydroxydodecyl) pyridinium compound as a white color material which was further dried at 50° C. in oven to get a white powder. The pyridine, 1,2-epoxydodecane, hydrochloric acid (37%), dichloromethane, and diethyl ether were purchased from Sigma-Aldrich.

Figure 3:
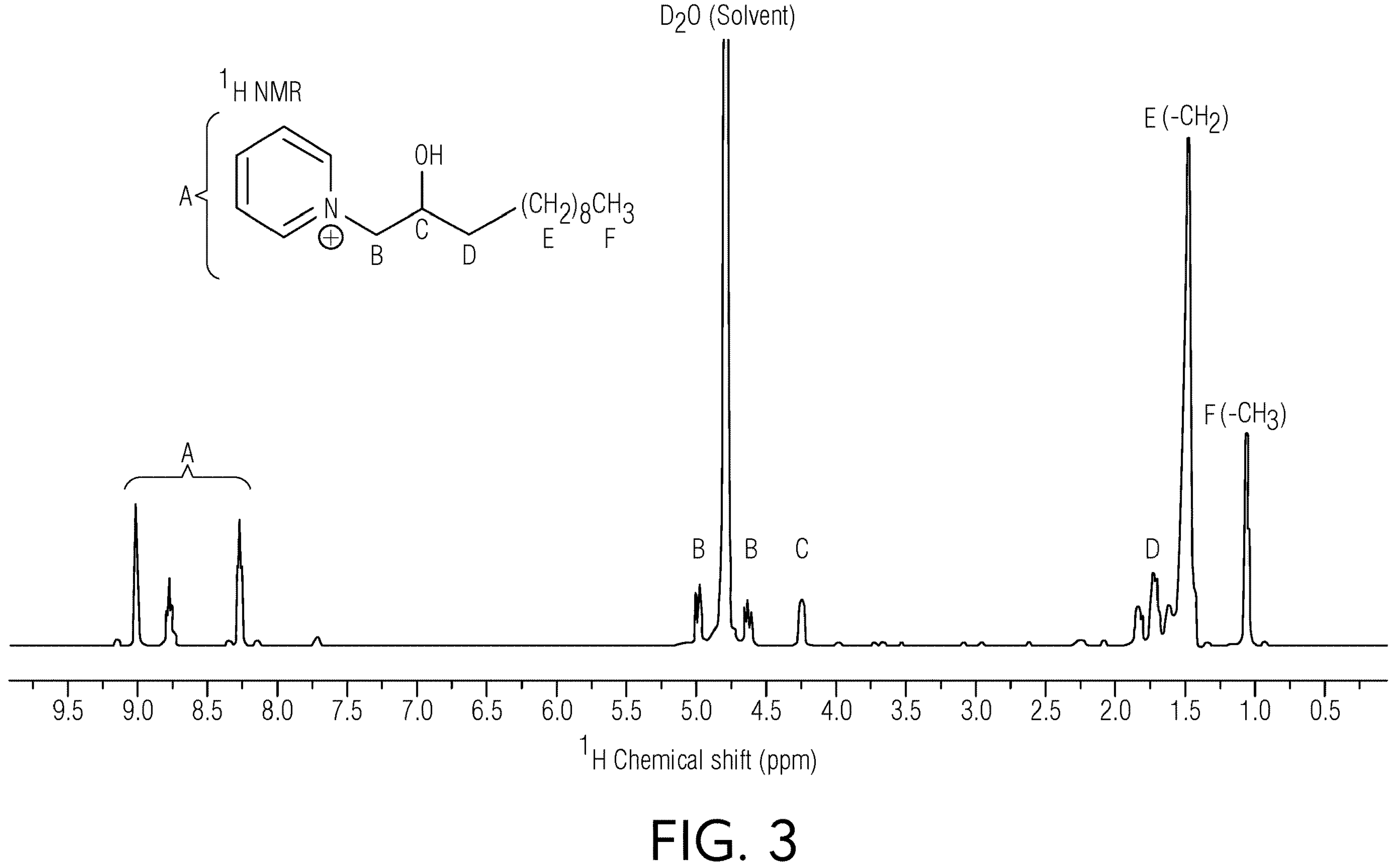
FIG. 3 graphically depicts the $^1H$ NMR spectrum of a synthesized 1-(2-hydroxyalkyl) pyridinium compound (1-(2-hydroxydodecyl)pyridinium chloride), according to one or more embodiments shown and described herein.
Figure 4:
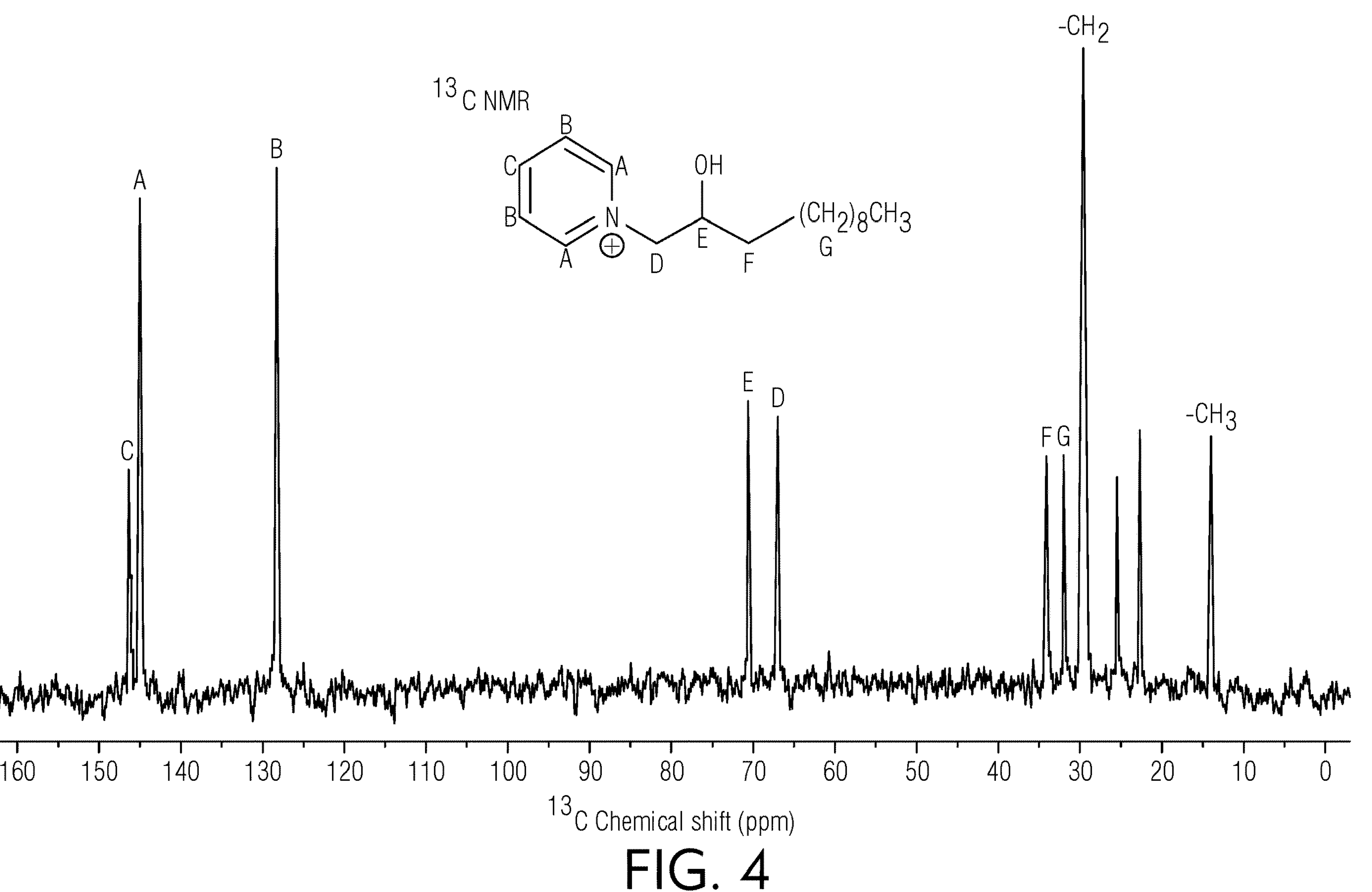
FIG. 4 graphically depicts the $^{13}C$ NMR spectrum of a synthesized 1-(2-hydroxyalkyl) pyridinium compound (1-(2-hydroxydodecyl)pyridinium chloride), according to one or more embodiments shown and described herein.

The synthesized polymers were characterized using $^1H$ and $^{13}C$ NMR spectroscopy. A Varian 500 MHz VNMRS spectrometer and a JEOL 500 MHz NMR spectrometer were utilized to obtain spectra using appropriate acquisition parameters. The NMR analyses were carried in deuterated water ($D_2O$) and deuterated trimethylsilyl propanoic acid (0 ppm) was used a reference for chemical shift. The $^1H$ NMR analysis confirmed the structures of the bis-quaternary ammonium compound. FIG. 3 provides the $^{1}H$ NMR spectrum and FIG. 4 provides the $^{13}C$ NMR spectrum of 1-(2-hydroxydodecyl)pyridinium chloride.

Example 2—Performance Evaluation of Corrosion-Resistant Materials

The ability of the 1-(2-hydroxyalkyl)pyridinium compounds disclosed herein to protect against corrosion was evaluated using the spindle test method described in NACE standard TM 0172. This standard test evaluates the performance of a corrosion inhibitor for petroleum product pipelines and involves rotating a steel test specimen at 1000 rpm while contacting the specimen with hydrocarbon, distilled water, and air.

Steel test specimens were prepared according to Table 1. The steel test specimens in Examples A-C were treated with one of the 1-(2-hydroxyalkyl)pyridinium compounds disclosed herein. The steel test specimen in Comparative Example A was treated with a non-hydroxylated 1-alkylpyridinium compound and the steel test specimen in Comparative Example B was treated with a known corrosion inhibitor, imidazoline. The steel test specimen in Comparative Example C was left untreated. All treated specimens were treated with a hydrocarbon-water solution of the test compound.

After a contact time of 4 hours at 38° C., each steel test specimen was examined for corrosion and the corrosion inhibition efficiency of the material was assessed. Each steel test specimen was given a rating as described in the NACE standard TM 0172 test method. A NACE rating of $B^{+}$ or better is generally required for transportation of hydrocarbon via pipeline. The corrosion inhibition efficiency of each corrosion inhibitor was calculated based on the percentage of the surface area of the steel test specimen that showed signs of corrosion. The results are shown in Table 1.

TABLE 1

| | Example A | Example B | Example C |
|---|---|---|---|
| *Corrosion Inhibitor | 1-(2-HDD)PC | 1-(2-HDD)PC | 1-(2-HTD)PC |
| Concentration Applied to Steel Test Specimen (ppm) | 100 | 20 | 100 |
| **NACE Rating | B | B | $B^{+}$ |
| Corrosion Inhibition Efficiency (%) | 89.03 (10.97% corroded surface area) | 80 (20% corroded surface area) | 98.98 (1.02% corroded surface area) |

*1-(2-HDD)PC = 1-(2-hydroxydodecyl)pyridinium chloride;
1-(2-HTD)PC = 1-(2-hydroxytetradecyl)pyridinium chloride;
**NACE Rating Scale: A = 0% surface area corrosion; $B^{++}$ = less than 0.1% surface area corrosion; $B^{+}$ = less than 5% surface area corrosion; B = 5% to 25% surface area corrosion; C = 25% to 50% surface area corrosion; D = 50% to 75% surface area corrosion; E = 75% to 100% surface area corrosion.

| | Comp. Example A | Comp. Example B | Comp. Example C |
|---|---|---|---|
| Corrosion Inhibitor | 1-dodecylpyridinium chloride | imidazoline | none |
| Concentration Applied to Steel Test Specimen (ppm) | 100 | 100 | N/A |
| **NACE Rating | C | D | E |
| Corrosion Inhibition Efficiency (%) | 50 (50% corroded surface area) | 37 (63% corroded surface area) | N/A (86% corroded surface area) |

TABLE 1-continued

**NACE Rating Scale: A = 0% surface area corrosion; $B^{++}$ = less than 0.1% surface area corrosion; $B^{+}$ = less than 5% surface area corrosion; B = 5% to 25% surface area corrosion; C = 25% to 50% surface area corrosion; D = 50% to 75% surface area corrosion; E = 75% to 100% surface area corrosion.

As shown in Table 1, the specimen treated with 100 ppm of 1-(2-hydroxydodecyl)pyridinium chloride was much less corroded (Example A, 10.97% corroded area) relative to the steel specimen with no corrosion inhibitor (Comparative Example C, 86% corroded area). The specimen treated with 100 ppm of 1-(2-hydroxytetradecyl)pyridinium chloride showed excellent resistance to corrosion (Example C, 1.02% corroded area).

The specimens treated with 1-(2-hydroxydodecyl)pyridinium chloride (Examples A and B, 89.03% and 70% corrosion inhibition efficiency, respectively) were significantly better protected against corrosion than was the specimen treated with the non-hydroxylated analog, 1-dodecylpyridinium chloride (Comparative Example A, 50% corrosion inhibition efficiency). This illustrates the significance of the 2-hydroxyl functionality in corrosion inhibition.

All specimens treated with the 1-(2-hydroxyalkyl)pyridinium compounds disclosed herein showed much less corrosion than the specimen treated with the known corrosion inhibitor, imidazoline (Comparative Example B, 37% corrosion inhibition efficiency). Even at a low dose, 1-(2-hydroxydodecyl)pyridinium chloride was far more protective against corrosion than was imidazoline (compare Example B to Comparative Example B).

The present disclosure includes one or more non-limiting aspects.

A first aspect includes a substrate comprising a first surface and a corrosion-resistant film positioned on at least a portion of the first surface of the substrate, wherein the corrosion-resistant film is solid, and wherein the corrosion-resistant film comprises a 1-(2-hydroxyalkyl)pyridinium compound having a general formula:

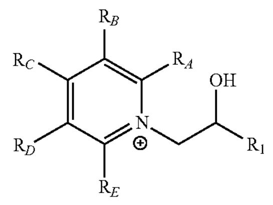

wherein: $R_1$ is a $C_1$-$C_{18}$ alkyl group, a $C_1$-$C_{18}$ hydroxyl alkyl group, a $C_1$-$C_{18}$ alkenyl group, a $C_1$-$C_{18}$ internal alkynl group, a $C_1$-$C_{18}$ acryl group, a $C_1$-$C_{18}$ cycloalkyl group, or a $C_1$-$C_{18}$ functional alkyl group; and $R_A$, $R_B$, $R_C$, $R_D$, and $R_E$ are each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group.

A second aspect includes any above aspect or combination of above aspects, wherein at least one of $R_1$, $R_A$, $R_B$, $R_C$, $R_D$, and $R_E$ is a $C_1$-$C_{18}$ functional alkyl group comprising a carboxyl group, an amine group, or a thiol group.

A third aspect includes any above aspect or combination of above aspects, wherein $R_1$ is selected from the group consisting of a $C_1$-$C_{18}$ alkyl group, $-CH_2CH_2OH$, and $-CH_2CH{=}CH_2$.

A fourth aspect includes any above aspect or combination of above aspects, wherein $R_1$ comprises a one or more of a carbon-carbon double bond, a carbon-carbon triple bond, or a combination thereof, provided that $R_1$ does not comprise a terminal alkyne.

A fifth aspect includes any above aspect or combination of above aspects, wherein $R_1$ is $-(CH_2)_9CH_3$ or $-(CH_2)_{11}CH_3$ and $R_A$, $R_B$, $R_C$, $R_D$, and $R_E$ are hydrogen.

A sixth aspect includes any above aspect or combination of above aspects, wherein the first surface is metal or metal oxide.

A seventh aspect includes any above aspect or combination of above aspects, wherein the substrate is a metal pipe and the first surface is an internal surface of the metal pipe.

An eighth aspect includes a corrosion inhibitor solution comprising a solvent and at least one 1-(2-hydroxyalkyl) pyridinium compound having the general formula:

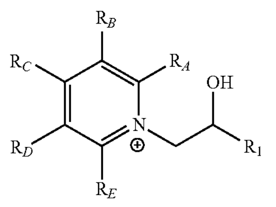

wherein: $R_1$ is a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group; and $R_A$, $R_B$, $R_C$, $R_D$, and $R_E$ are each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group.

A ninth aspect includes any above aspect or combination of above aspects, wherein the solvent comprises water, an alcohol, aromatic naphtha, or any combination of these.

A tenth aspect includes any above aspect or combination of above aspects, wherein the at least one 1-(2-hydroxyalkyl)pyridinium compound comprises from 1.0 wt % to 50 wt % of the corrosion inhibitor solution.

An eleventh aspect includes any above aspect or combination of above aspects, wherein: $R_1$ is $-(CH_2)_9CH_3$ or $-(CH_2)_{11}CH_3$; $R_A$, $R_B$, $R_C$, $R_D$, and $R_E$ are hydrogen; and the 1-(2-hydroxyalkyl)pyridinium compound comprises from 20 wt % to 30 wt % of the corrosion inhibitor solution.

A twelfth aspect includes a method of producing a corrosion-resistant substrate, the method comprising: contacting at least a portion of a first surface of a substrate with a corrosion inhibitor solution comprising: a solvent; and from 1.0 wt % to 50 wt % of at least one 1-(2-hydroxyalkyl) pyridinium compound having the general formula:

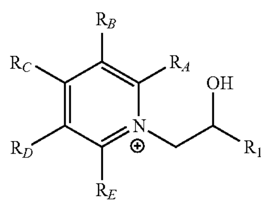

wherein: $R_1$ is a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group; and $R_A$, $R_B$, $R_C$, $R_D$, and $R_E$ are each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, a $C_1$-$C_{18}$ cycloalkyl group, or a $C_1$-$C_{18}$ functional alkyl group; and drying the corrosion inhibitor solution to produce the corrosion-resistant film on the substrate, wherein at least a portion of the solvent is expelled from the corrosion inhibitor solution during the drying to form the corrosion-resistant film, such that the corrosion-resistant film is solid.

A thirteenth aspect includes the method of the twelfth aspect, wherein the corrosion inhibitor solution comprises: from 70 wt % to 80 wt % of at least one solvent selected from the group consisting of water, an alcohol, and aromatic naphtha; and from 20 wt % and 30 wt % of the at least one 1-(2-hydroxyalkyl)pyridinium compound.

A fourteenth aspect includes the method of the twelfth or thirteenth aspects or combinations thereof, wherein $R_A$, $R_B$, $R_C$, $R_D$, and $R_E$ are hydrogen and $R_1$ is either $-(CH_2)_9CH_3$ or $-(CH_2)_{11}CH_3$.

A fifteenth aspect includes the method of the twelfth through fourteenth aspects or combinations thereof, wherein $R_1$ is $-CH_2-CH_2-OH$ or $-CH_2CH{=}CH_2$.

A sixteenth aspect includes the method of the twelfth through fifteenth aspects or combinations thereof, wherein at least one of $R_1$, $R_A$, $R_B$, $R_C$, $R_D$, and $R_E$ is a $C_1$-$C_{18}$ alkyl group or a $C_1$-$C_{18}$ functional alkyl group comprising a carboxyl group, an amine group, or a thiol group.

A seventeenth aspect includes the method of the twelfth through sixteenth aspects or combinations thereof, wherein the first surface of the substrate is metal or metal oxide.

An eighteenth aspect includes the method of the twelfth through seventeenth aspects or combinations thereof, wherein the substrate is a metal pipe and the first surface is an internal surface of the metal pipe.

A nineteenth aspect includes the method of the twelfth through eighteenth aspects or combinations thereof, wherein: $R_1$ is $-(CH_2)_9CH_3$; $R_A$, $R_B$, $R_C$, $R_D$, and $R_E$ are hydrogen; and the 1-(2-hydroxyalkyl)pyridinium compound comprises from 20 wt % to 30 wt % of the corrosion inhibitor solution.

A twentieth aspect includes the method of the twelfth through nineteenth aspects or combinations thereof, wherein the at least one 1-(2-hydroxyalkyl)pyridinium compound is formed by reacting pyridine, optionally substituted with one or more substituents, and an $R_1$-substituted epoxide, according to the reaction scheme:

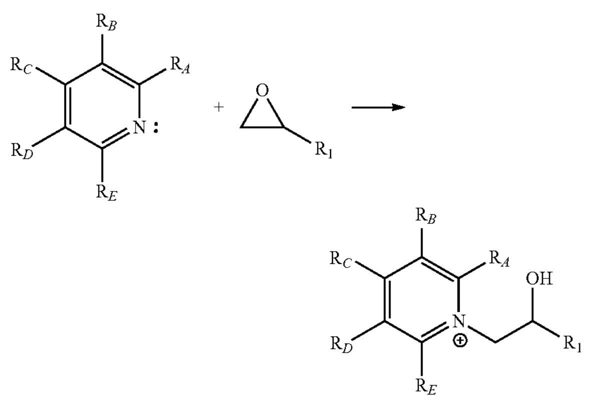

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

It is also noted that recitations herein of "at least one" component, element, etc., should not be used to create an inference that the alternative use of the articles "a" or "an" should be limited to a single component, element, etc.

For the purposes of describing and defining the presently disclosed technology it is noted that the terms "substantially" and "about" are utilized herein to represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

What is claimed is:

1. A corrosion-resistant substrate comprising:

a substrate comprising a first surface; and a corrosion-resistant film positioned on at least a portion of the first surface of the substrate, wherein the corrosion-resistant film is solid, and wherein the corrosion-resistant film comprises a 1-(2-hydroxyalkyl) pyridinium compound having a general formula:

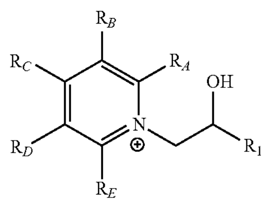

wherein:

$R_1$ is a $C_1$-$C_{18}$ alkyl group, a $C_1$-$C_{18}$ hydroxyl alkyl group, a $C_1$-$C_{18}$ alkenyl group, a $C_1$-$C_{18}$ internal alkynl group, a $C_1$-$C_{18}$ acryl group, or a $C_1$-$C_{18}$ cycloalkyl group; and $R_A$, $R_B$, $R_C$, $R_D$, and $R_E$ are each independently chosen from hydrogen, a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, a $C_1$-$C_{18}$ acryl group, or a $C_1$-$C_{18}$ cycloalkyl group.

2. The corrosion-resistant substrate of claim 1, wherein $R_1$ is selected from the group consisting of a $C_1$-$C_{18}$ alkyl group, $-CH_2CH_2OH$, and $-CH_2CH{=}CH_2$.

3. The corrosion-resistant substrate of claim 1, wherein $R_1$ comprises one or more of a carbon-carbon double bond, a carbon-carbon triple bond, or a combination thereof, provided that $R_1$ does not comprise a terminal alkyne.

4. The corrosion-resistant substrate of claim 1, wherein $R_1$ is $-(CH_2)_9CH_3$ or $-(CH_2)_{11}CH_3$ and $R_A$, $R_B$, $R_C$, $R_D$, and $R_E$ are hydrogen.

5. The corrosion-resistant substrate of claim 1, wherein the first surface is metal or metal oxide.

6. The corrosion-resistant substrate of claim 1, wherein the substrate is a metal pipe and the first surface is an internal surface of the metal pipe.

7. A method of producing the corrosion-resistant substrate of claim 1, the method comprising:

contacting the portion of the first surface of the substrate with a corrosion inhibitor solution comprising:

a solvent; and from 1.0 wt % to 50 wt % of the 1-(2-hydroxyalkyl) pyridinium compound; and drying the corrosion inhibitor solution to produce the corrosion-resistant film on the substrate, wherein at least a portion of the solvent is expelled from the corrosion inhibitor solution during the drying to form the corrosion-resistant film, such that the corrosion-resistant film is solid.

8. The method of claim 7, wherein the corrosion inhibitor solution comprises:

from 70 wt % to 80 wt % of at least one solvent selected from the group consisting of water, an alcohol, and aromatic naphtha; and from 20 wt % and 30 wt % of the at least one 1-(2-hydroxyalkyl) pyridinium compound.

9. The method of claim 7, wherein $R_A$, $R_B$, $R_C$, $R_D$, and $R_E$ are hydrogen and $R_1$ is either $-(CH_2)_9CH_3$ or $-(CH_2)_{11}CH_3$.

10. The method of claim 7, wherein Riis-$CH_2CH_2OH$, or $-CH_2CH{=}CH_2$.

11. The method of claim 7, wherein $R_1$ is a $C_1$-$C_{18}$ alkyl group.

12. The method of claim 7, wherein the first surface of the substrate is metal or metal oxide.

13. The method of claim 7, wherein the substrate is a metal pipe and the first surface of the substrate is an internal surface of the metal pipe.

14. The method of 12, wherein:

$R_1$ is $-(CH_2)_9CH_3$ or $-(CH_2)_{11}CH_3$;

$R_A$, $R_B$, $R_C$, $R_D$, and $R_E$ are hydrogen; and the 1-(2-hydroxyalkyl) pyridinium compound comprises from 20 wt % to 30 wt % of the corrosion inhibitor solution.

15. The method of claim 7, wherein the at least one 1-(2-hydroxyalkyl) pyridinium compound is formed by reacting pyridine, optionally substituted with one or more substituents, and an $R_1$-substituted epoxide, according to the reaction scheme:

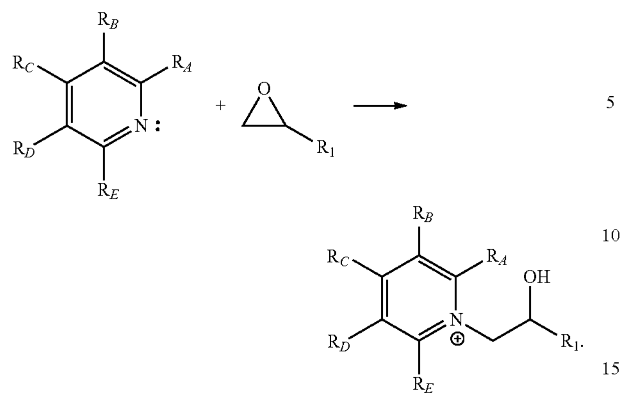
* * * * *